United States Patent
Roizin et al.

(10) Patent No.: US 12,332,115 B2
(45) Date of Patent: Jun. 17, 2025

(54) ULTRAVIOLET C (UVC) DETECTION

(71) Applicant: Tower Semiconductor Ltd., Migdal Haemek (IL)

(72) Inventors: Yakov Roizin, Afula (IL); Pikhay Evgeny, Haifa (IL); Michael Yampolsky, Haifa (IL)

(73) Assignee: Tower Semiconductor Ltd., Migdal Haemek (IL)

( * ) Notice: Subject to any disclaimer, the term of this patent is extended or adjusted under 35 U.S.C. 154(b) by 464 days.

(21) Appl. No.: 17/659,171

(22) Filed: Apr. 13, 2022

(65) Prior Publication Data

US 2023/0332947 A1  Oct. 19, 2023

(51) Int. Cl.
*A61L 2/10* (2006.01)
*G01J 1/42* (2006.01)
*G01J 1/44* (2006.01)

(52) U.S. Cl.
CPC ............. *G01J 1/429* (2013.01); *A61L 2/10* (2013.01); *G01J 1/44* (2013.01); *A61L 2202/14* (2013.01)

(58) Field of Classification Search
CPC ..... G01J 1/429; G01J 1/44; A61L 2/10; A61L 2202/14
See application file for complete search history.

(56) References Cited

U.S. PATENT DOCUMENTS

2022/0143250 A1*  5/2022  Pierson .................. G05D 1/689

FOREIGN PATENT DOCUMENTS

DE  112021001473 T5 *  1/2023  ............ A61L 2/10
RU  2627929 C2 *  8/2017  ......... A61B 6/4233

* cited by examiner

*Primary Examiner* — Dani Fox
*Assistant Examiner* — Fani Polyzos Boosalis
(74) *Attorney, Agent, or Firm* — Reches Patents

(57) ABSTRACT

A UVC disinfection system that may include a UVC radiation illumination unit, a control unit, and a node. The node may include (i) a power supply, (ii) a UVC dose sensing unit that comprises a UVC sensing element, wherein the UVC dose sensing unit is configured to sense that the UVC radiation dose received by the node reached a predefined UVC radiation dose; and (iii) a node transmitter that is configured transmit a node unique signal following a sensing, by the UVC dose sensing unit, that the UVC radiation dose received by the node reached a predefined UVC radiation dose. The control unit is configured to control an emission of UVC radiation from the UVC radiation illumination unit based on a reception or a lack of reception of the node unique signal.

20 Claims, 12 Drawing Sheets

ULTRAVIOLET C (UVC) DETECTION

BACKGROUND OF THE INVENTION

Ultraviolet C (UVC) radiation with wavelength that ranges between two hundred nanometers and two hundred eighty nanometer is used for sanitizing against coronavirus (Covid-19) and other microorganisms.

Current sterilization method define time limits for applying UVC radiation during sterilization. These time limits are inaccurate.

There is a growing need to provide a system and a method for accurate UVC sterilization.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
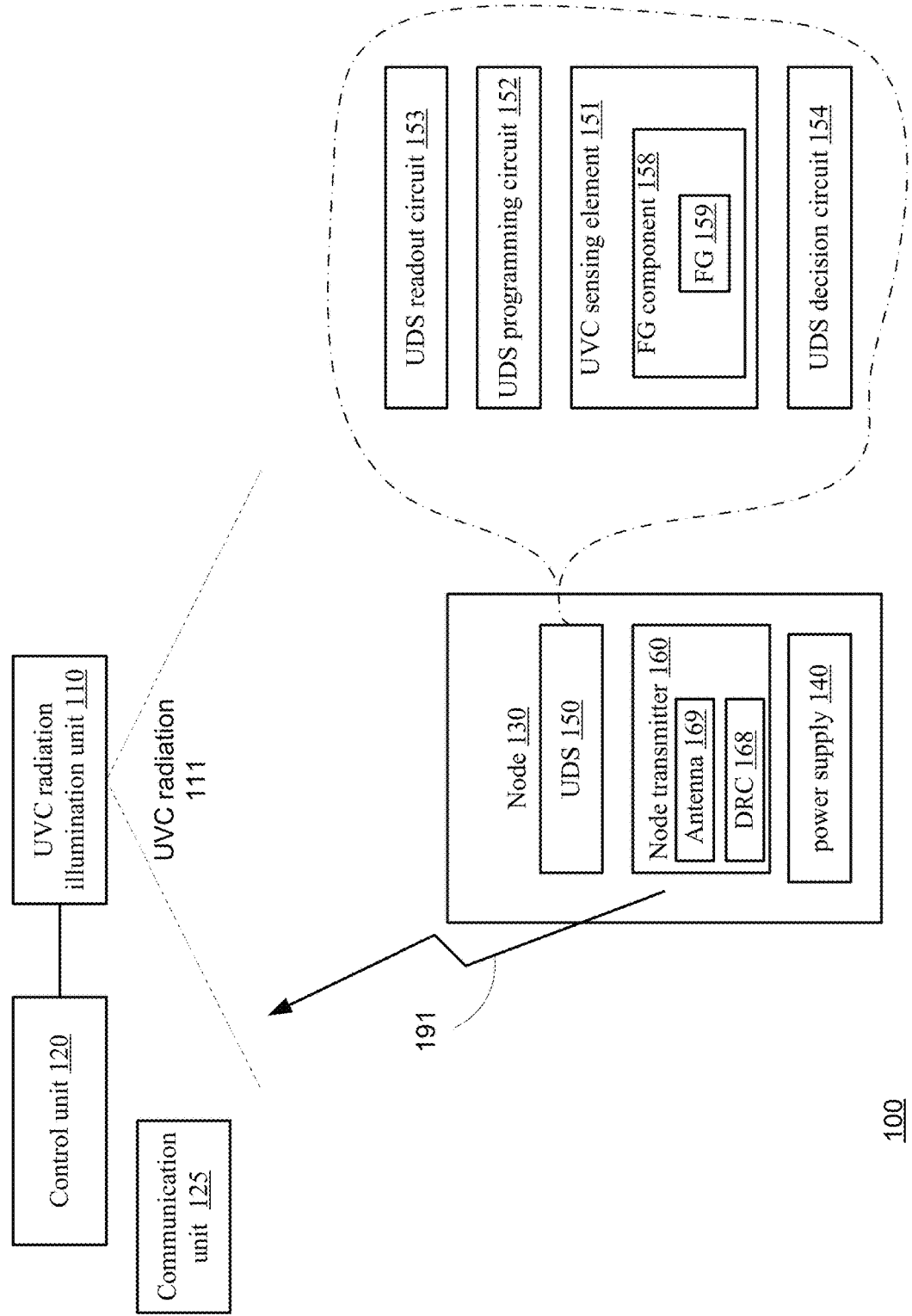
FIG. 1 is an example of a UVC disinfection system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF THE PREFERRED EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

The term "and/or" means additionally or alternatively. For example—A and/or B—may mean only A, only B, or both A and B.

Any reference to a method should be applied mutatis mutandis to a robust analog counter and/or a module that includes the robust analog counter configured to execute the method.

Any reference to a robust analog counter and/or a module that includes the robust analog counter should be applied mutatis mutandis to a method executable by the robust analog counter and/or a module that includes the robust analog counter.

There may be provided a method for UVC disinfection, a UVC disinfection system and a node for accurately disinfecting objects.

Referring, for simplicity of explanation, to the system—the system may include a node that senses when the node was exposed to a predefined UVC radiation dose. The exposure may be measured during a sensing period. The predefined UVC dose is enough for disinfecting the object. When this event occurs (exposure to the predefined UVC radiation dose during the sensing period)—the node transmits a node unique signal which can be used to stop the disinfection process.

The system may include multiple nodes that are configured to send node unique signals. Thus—any reference to a node may be applied mutatis mutandis to a group of more one nodes.

FIG. 1 illustrates an example of UVC disinfection system 100.

UVC disinfection system 100 includes UVC radiation illumination unit 110 (that radiates UVC radiation 111), control unit 120 and one or more nodes such as node 130.

The UVC radiation illumination unit 110 and the control unit 120 may be packaged together, or may be located at different locations—that are close to each other or distance from each other.

Node 130 may include power supply 140, a UVC dose sensing unit, and node transmitter 160.

The UVC dose sensing unit (referred to as USR 150) may be configured to sense that the UVC radiation dose received by the node reached a predefined UVC radiation dose.

UDS 150 may include a UVC sensing element 151, a UDS programming circuit 152, a UDS readout circuit 153, and UDS decision circuit 154.

The UVC sensing element 151 may be ignorant (due to structure, materials, one or more internal radiation shields and/or one or more external radiation shields) to radiation other than UVC radiation—for example may be ignorant to visible light. This feature increases the accuracy of the measurement of UVC radiation dose.

The UVC sensing element 151 may be or may include a transistor, a diode, may be formed in silicon, may be a silicon UVC sensing element, may be a composite material UVC sensing element, and the like.

The UVC sensing element 151 may be a floating gate (FG) component 158 that includes a floating gate 159. The potential of the FG 159 ("FG potential") may be probed in any manner—for example by measuring a voltage that is indicative of the FG potential.

The UDS programming circuit 152 may be configured to set the FG potential to a start value at a start of a sensing period. The setting of the FG potential may be performed at a beginning of the sensing period. The FG potential may decrease when exposed to the UVC radiation and the start value may be higher than then a FP potential when the UVC radiation dose received by the node reaches the predefined UVC radiation dose. The start value may be determined in any manner.

UDS readout circuit 153 may be configured to read FG 159 and output a voltage that is indicative of the FG potential.

UDS decision circuit 154 may determine, based on the voltage that is indicative of the FG potential, when the node was exposed, during the sensing period, to the predefined UVC radiation dose.

UDS readout circuit 153 and UDS decision circuit 154 can be combined, may share at least one component or may be separate circuits.

The node transmitter 160 is configured to transmit a node unique signal 191 following a sensing, by the UVC dose sensing unit 150, that the UVC radiation dose received by the node reached a predefined UVC radiation dose.

The control unit 120 may be configured to control an emission of UVC radiation from the UVC radiation illumination unit based on a reception or a lack of reception of the node unique signal.

For example—the control unit 120 may be configured to stop the UVC radiation emission following a reception of the node unique signal.

It should be noted that the UVC radiation emission may start in various manners—may be controlled manually by a user, may be location conditioned (for example may start when reaching a certain location), may start following a detection of the node, and the like.

The UVC radiation emission may be executed constantly, or non-constantly.

The node unique signal may be a node identifier—for example may be a radio frequency identification (RFID) identifier. The node unique signal may not identify the node.

The node transmitter 160 may include an antenna 168 and a driving circuit 169 (denoted "DRC") of any kind. The driving circuit 169 may belong to a node communication unit. The node transmitter 160 may obtain the node unique signal (or may obtain node unique signal information that is converted to the node unique signal).

The node transmitter 160 may be a RFID transmitter and the node unique signal may be an RFID code. In this case the UVC disinfection system may include a RFID reader that may be in communication with the control unit.

The node transmitter 160 may differ from an RFID transmitter and the node unique signal may be a non-RFID compliant signal.

Power supply 140 may be a battery. The node may be electrically connected to a power grid that is not a part of the node. Alternatively—the power supply 140 may be a UVC radiation based power supply that may be configured to convert UVC radiation to electrical power.

Node 130 may be or may include a system on chip (SoC). The node may include one or more capacitors that may be used for storing change for powering various components of the node. The capacitors may be bonded to the SoC or may be included in the SOC. The node may include one or more integrated circuits. The node may differ from a SoC. The node may include a housing or any other mechanical element used to protect the node and/or to fasten the node or connect the node to its environment.

The node may be fabricated in CMOS technology—which reduces the cost of the node.

The node may be fabricated using Radio Frequency Silicon on Insulator (RF-SOI) technology—and benefit from having high voltage UVC to electrical power converting elements that are used for UVC based power supply.

The UVC source may be of any type—for example may be a UVC gas-filled lamp or a UVC light emitting diode.

FIG. 1 also illustrates communication unit 125 that belongs to the system and is configured to receive signals transmitted from the node. The communication unit 125 may be a stand-alone unit, may be included in the control unit 120 and/or in the UVC radiation illumination unit 110. The UVC radiation illumination unit 110 and the control unit 120 may communicate with each other—or at least the UVC radiation illumination unit 110 may be configured to receive commands from the control unit 120. The communication unit may be capable to communicate in any manner—wired or wireless, and in use any protocol and/or using any conveying signals of any frequency.

The UVC radiation illumination unit 110 may receive the node unique signal and stop the illumination.

Figure 2:
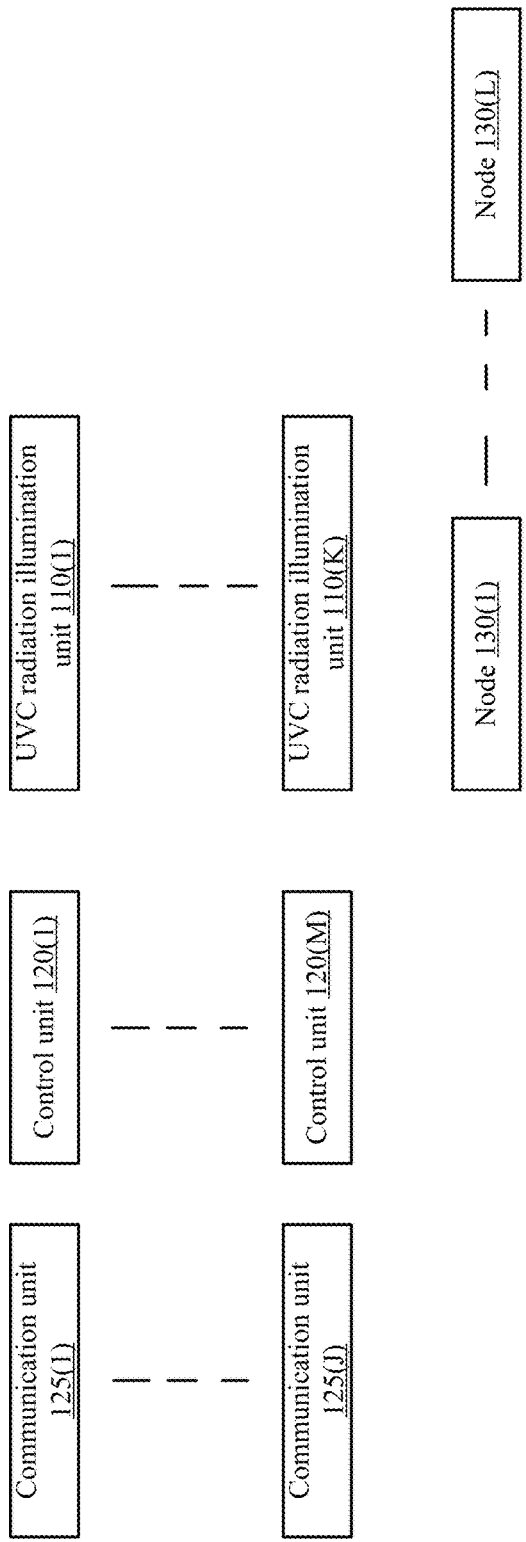
FIG. 2 is an example of a UVC disinfection system.

FIG. 2 illustrates an example of UVC disinfection system 101.

UVC disinfection system 101 includes UVC radiation illumination unit 110(1)-110(K), control units 120(1)-120(M), nodes 130(1)-130(L) and communication units 125(1)-125(J). K, J and L are integers that exceed one. At least two of L, J, K and M may differ from each other or may be equal to each other. A UVC disinfection system 101 multiple nodes but a single control unit (illustrated in FIG. 3—see control unit 120) and/or a single UVC radiation illumination unit (also illustrated in FIG. 3—see UVC radiation illumination unit 110). A UVC disinfection system may include a single node and/or a single control unit but have multiple UVC radiation illumination units, and the like.

For simplicity of explanation it is assumed to nodes 130(1)-130(L) are the same as node 30 of FIG. 1. Nevertheless—any node may be the same as any other node illustrated in the application. All nodes may be the same. Alternatively—one node may differ from another node.

Each node of the group of nodes that includes nodes 130(1)-130(L) is configured to transmit a node unique signal following a sensing, by a UVC dose sensing unit of the node, that the UVC radiation dose received by the node reached the predefined UVC radiation dose. Different nodes of the group are configured to transmit node unique signals that differ from each other.

Control units 120(1)-120(M) may be configured to control the emission of UVC radiation from the UVC radiation illumination unit based on a reception or a lack of reception of node unique signals from at least some of the nodes of the group.

For example—the control units may be configured to stop the UVC radiation emission following a reception of a node unique signal from each node of the group.

Alternatively—the control units may be configured to stop the UVC radiation emission following a reception of a node unique signal from at least a predefined number node of the group or from at least a predefined percentage (for example 70, 75, 80, 85, 90, 95, 99 percent and the like) of nodes of the group. The predefined number and/or the predefined percentage may be set in any manner—for example by a user, automatically, and the like.

Figure 3:
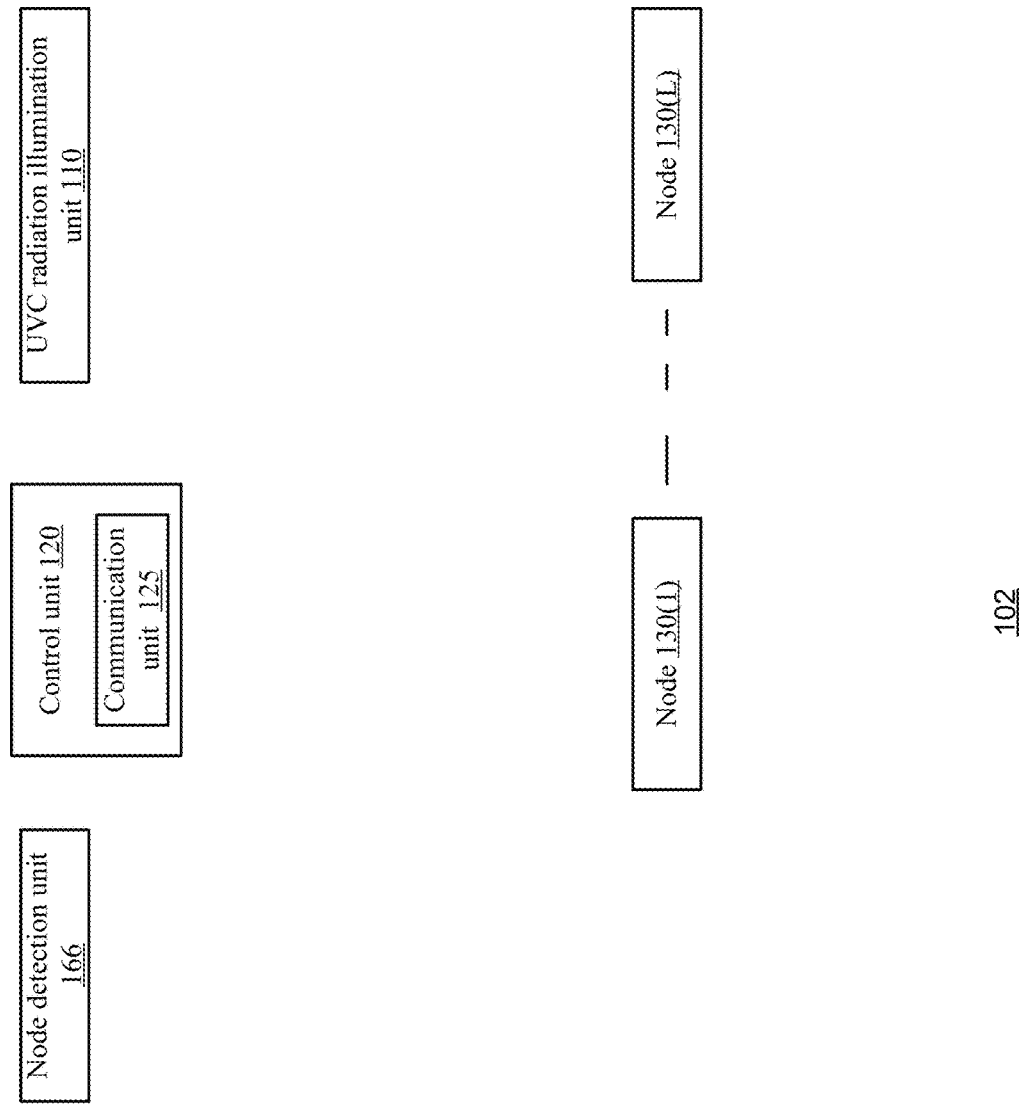
FIG. 3 is an example of a UVC disinfection system.

FIG. 3 illustrates an example of UVC disinfection system 102.

UVC disinfection system 102 includes UVC radiation illumination unit 110, control unit 120, nodes 130(1)-130(L), and node detection unit 166. In FIG. 3 the control unit 120 includes a communication unit 125. The UVC radiation illumination unit 110 may have its own communication unit (not shown).

Node detection unit 166 may be configured to detect a presence of the node when the node operated in a passive mode. Passive mode—when the node does not transmit the node unique signal—for example when the node is idle or disactivated, without power, and the like.

The node detection unit 166 may impact the control of the UVC radiation illumination unit 110. Control unit 120 may be configured to control the emission of UVC radiation from UVC radiation illumination unit 110 also in response to a detection or a lack of detection of the node.

For example—control unit 120 may be configured to start the UVC radiation emission following a detection of the node.

The node detection unit may include a radio frequency identification (RFID) reader—but may use any other technology to detect the node.

Figure 4:
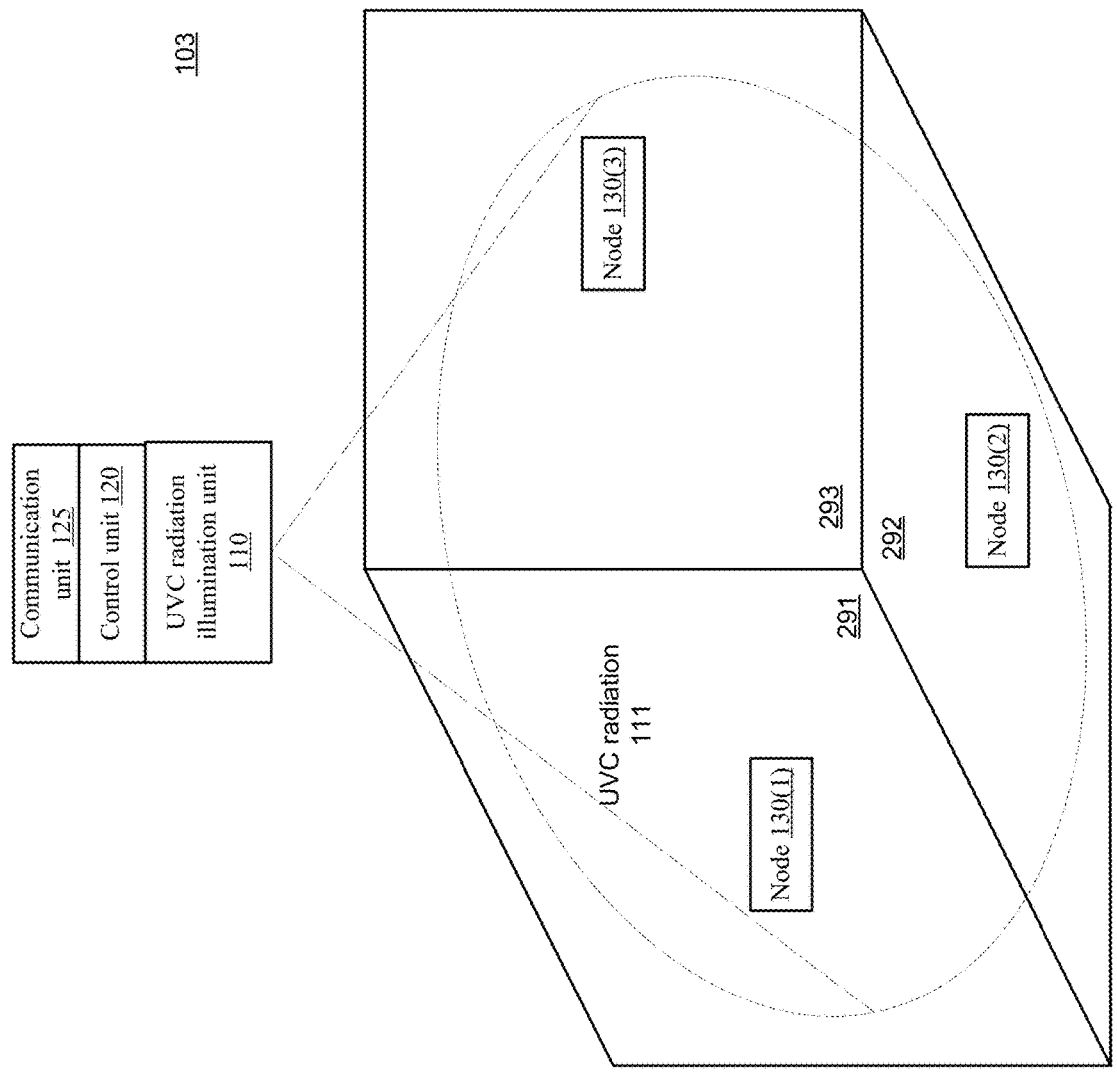
FIG. 4 is an example of a UVC disinfection system and of a disinfection process.

FIG. 4 illustrates an example of UVC disinfection system 103 that disinfects an objects that has three facets 291, 292 and 293. The UVC disinfection system 103 has first node 130(1) attached to the first facet 291, second node 130(2) attached to the second facet 292 and third node 130(3) that is attached to the third facet 293. In FIG. 4 the UVC radiation illumination unit 110 illuminates (see "UVC radiation 111") parts of all three facets simultaneously and exposes all three nodes to UVC radiation.

In FIG. 4 the communication unit 125, the control unit 120 and the UVC radiation illumination unit 110 are packaged together.

Figure 5:
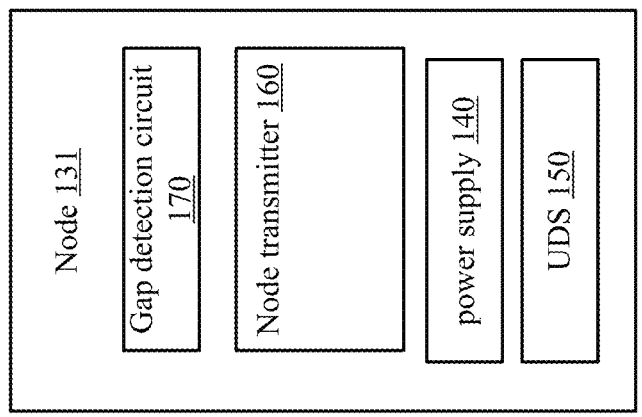
FIG. 5 is an example of a node.

FIG. 5 illustrates an example of node 131.

Node 131 may include power supply 140, UVC dose sensing unit 150, node transmitter 160 as well as a time gap (further mentioned as "gap") detection circuit 170 that may be configured to detect a gap when there was no UVC radiation at the dose sensing unit 150—and especially determine whether the duration of the gap exceeds a threshold. When the gap exceeds the threshold it may be assumed that continuing the UVC irradiation after the gap is ineffective and that the emission of the UVC radiation prior the gap should be ignored in the disinfection process.

When the duration of the gap exceeds a threshold, then the disinfection process should restart, a new sensing period may begin, and the nodes should receive (following the restart) the full predefined UVC radiation dose.

Accordingly—when gap detection circuit 170 detects that the duration of the gap exceeds the threshold—there is a need to restart the sensing that the UVC radiation dose received by the node reached the predefined UVC radiation dose. An indication about the gap may or may not be sent to the control unit. In the following example such an indication is not shown.

Any reference to a gap may be applied mutatis mutandis to multiple gaps that are shorter than the threshold—but their sum may exceed a threshold.

Figure 6:
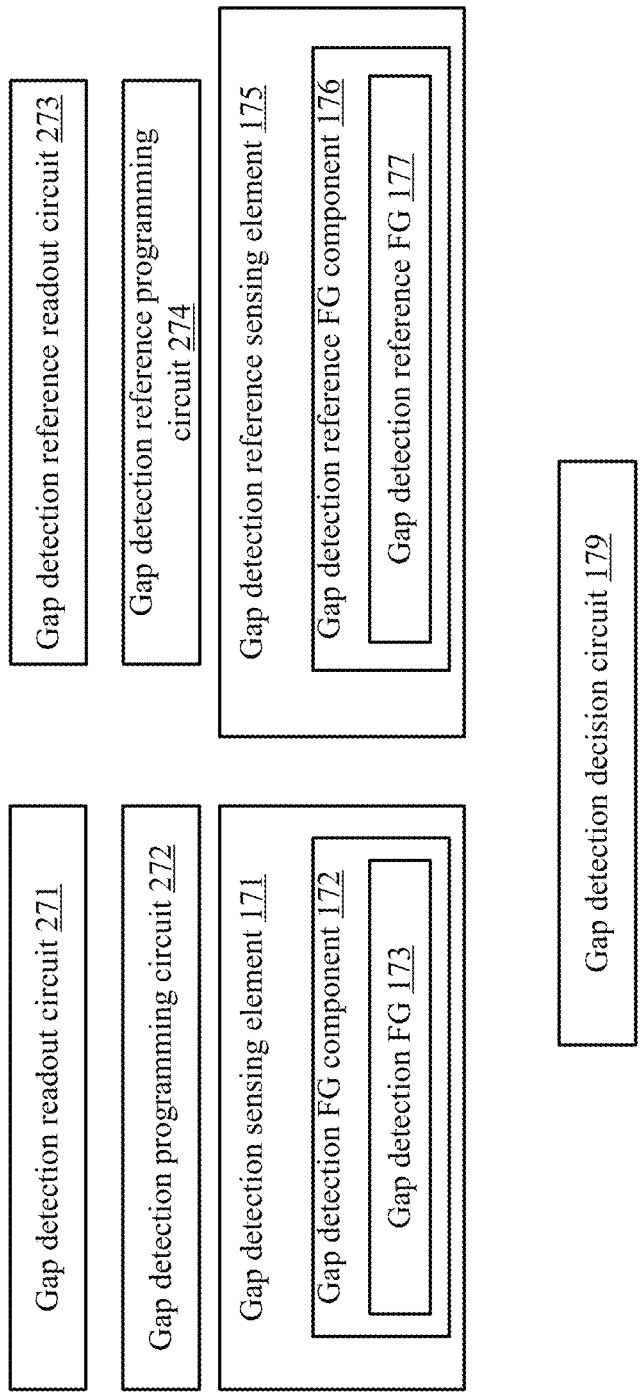
FIG. 6 is an example of a gap detection unit.

FIG. 6 illustrates an example of gap detection circuit 170.

The gap detection circuit 170 may include (a) gap detection sensing element 171 that may include gap detection FG component 172 that includes gap detection FG 173, (b) gap detection reference sensing unit 175 that includes gap detection reference FG component 176 that include gap detection reference FG 177, (c) gap detection decision circuit 179, (d) gap detection readout circuit 271 and gap detection programming circuit 272—for programming and reading the gap detection FG 173, and (e) gap detection reference readout circuit 273 and gap detection reference programming circuit 274—for programming and reading the gap detection reference FG 177.

The gap detection reference FG component 176 is ignorant (due to structure, materials, one or more internal UVC shields and/or one or more external UVC shields) to the UVC radiation. An external UVC shield may be located outside the gap detection reference sensing unit 175, outside semiconductor layers that form the gap detection reference sensing unit 175, and the like.

The charge retention of gap detection reference FG component 176 (for example—time when its FG potential decreases more than 10 mV to allow reliable measurement of its change) is in the range from 0.1 sec to 5000 sec. The lower retention rate of the gap detection reference polysilicon FG component 176 may be obtained by electrically coupling the gap detection reference FG to a metal layer of the gap detection circuit. The coupling can be done by using a metal trace, a VIA, or any other coupling element connected to the FG.

The gap detection decision circuit 179 may be configured to determine that the duration of the gap exceeds the threshold based on a difference between a potential of gap detection FG 173 and the potential of gap detection reference FG 177.

Figure 7:
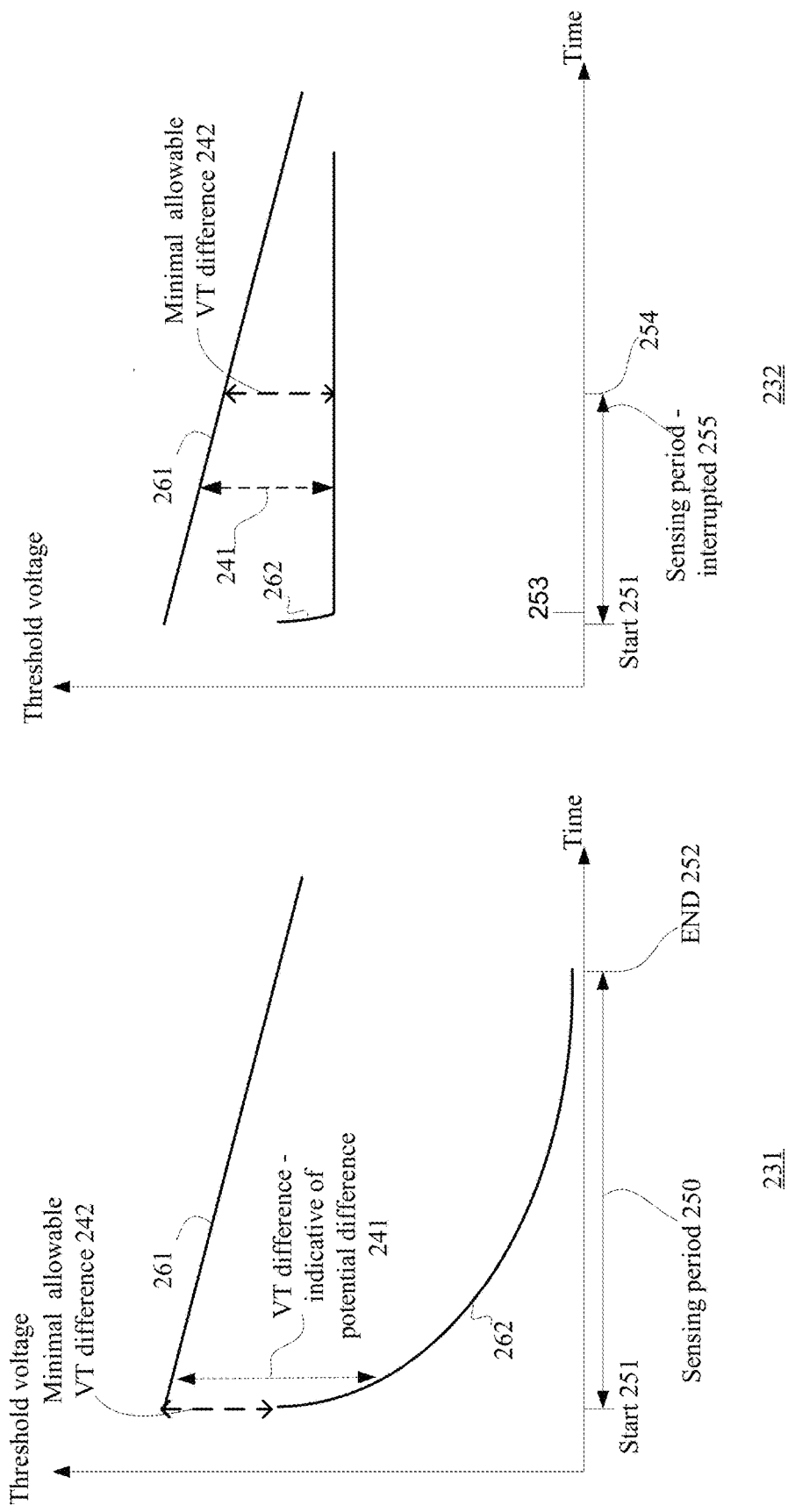
FIG. 7 illustrates examples of an uninterrupted sensing period and of an interrupted sensing period.

FIG. 7 illustrates examples of an uninterrupted sensing period 250 and of an interrupted sensing period 255.

FIG. 7 illustrates a first example 231 and a second example 232 of a threshold voltage of gap detection reference FG 177 and of a threshold voltage of gap detection FG 173.

First example 231 illustrates an uninterrupted sensing period 250 between a start 251 point of time and an END point of time 252 in which the node reaches an exposure to the predefined UVC radiation dose.

In the first example 231, threshold voltage of gap detection FG 173 decreases (curve 262) as the gap detection FG 173 is exposed to UVC radiation. The decrease of the threshold voltage of gap detection FG 173 (once exposed to the UVC radiation) is steeper than the decrease (see curve 261) of the threshold voltage of gap detection reference FG 177—and the difference (241) between these threshold voltages exceeds, during the sensing period the minimal allowable threshold voltage difference 242.

In the second example 232, threshold voltage of gap detection FG 173 decreases (curve 262)—from start time 251 until time 253 in which the UVC radiation stops. From point in time 253 the threshold voltage of gap detection FG 173 barely decreases (or decreases at a lower rate than the decrease of the threshold voltage of gap detection reference FG 177. At point of time 254 the difference (241) between these threshold voltages is below the minimal allowable threshold voltage difference 242—the gap is detected and the sensing period is declared as an interrupter sensing period.

In both cases one the illumination is stopped for enough time the node may be reset.

Figure 8:
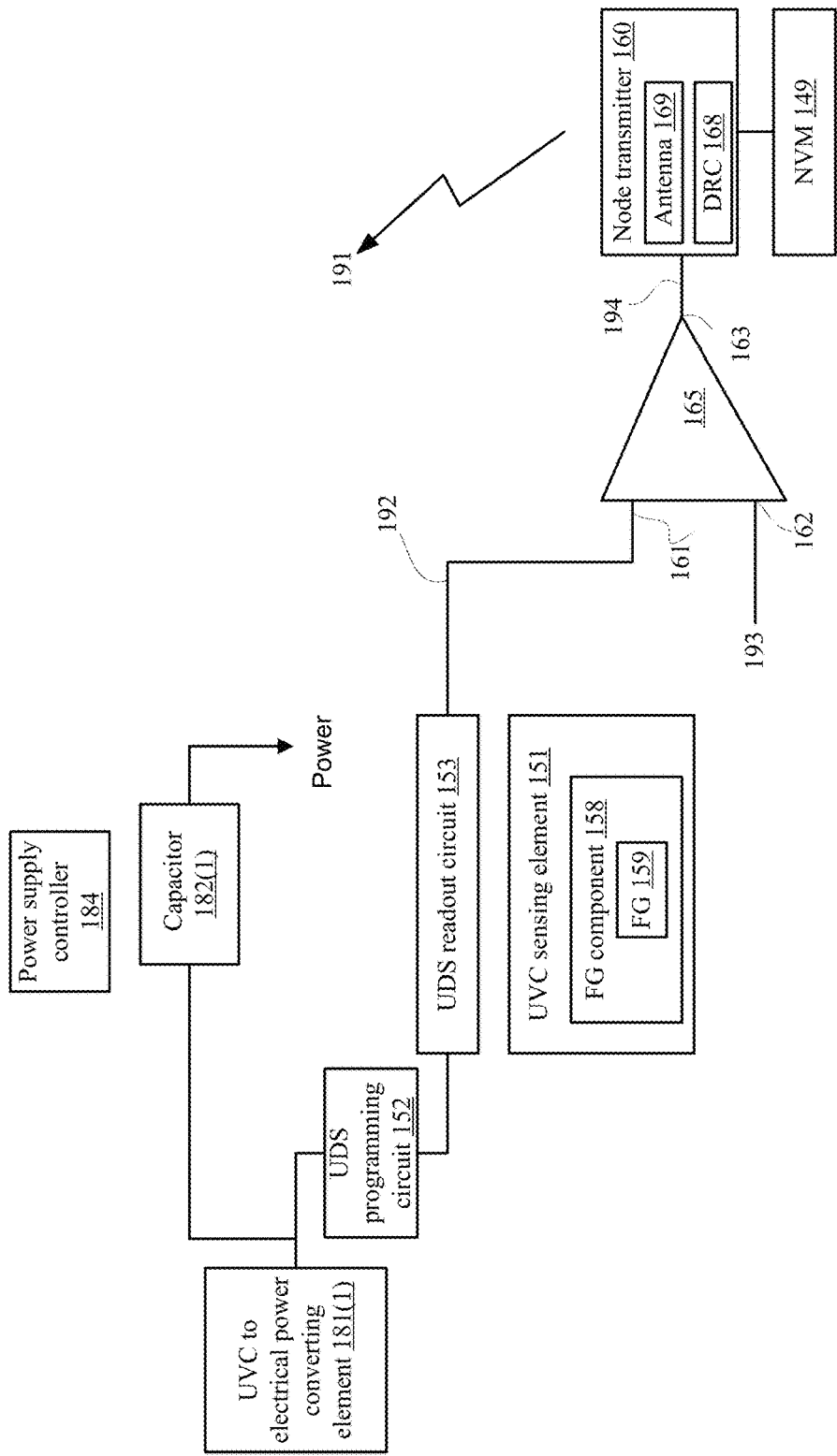
FIG. 8 is an example of a node.

FIG. 8 illustrates an example of node 132.

Node 132 includes power supply 140, UDS 150 (including UDS programming circuit 152, UVC sensing element 151 that is a FG component that includes a FG 159), node transmitter 160, comparator 165 (having a first input 161, a second input 162 and an output 163), and a node memory.

The comparator 165 is configured to compare a voltage 192 indicative of the potential of the FG (the voltage is received at the first input 161), to a reference voltage 193.

The reference voltage 193 may equal the value of voltage 192 when the FG potential reaches a RF reference potential that indicates that the UVC sensing unit was exposed to predefined UVC radiation dose.

When voltage 192 reaches the reference voltage the comparator 165 is configured to output (via output 163) a comparator output signal 194 that is indicative that the FG potential reached a reference potential.

The node transmitter is configured to transmit the node unique signal following the generation of the comparator output signal that is indicative that the FG potential reached the reference potential.

The power supply 140 is UVC radiation based power supply.

FIG. 8 illustrates a node memory such as a non-volatile memory 149. The non-volatile memory 149 is configured to store node unique signal information that may be converted by the node to the node unique signal 191. The node may include a memory unit other than the non-volatile memory 149.

It should be noted that the node memory may exist in a node that has a power supply that differs from a UVC radiation based power supply.

The UAV radiation based power supply includes a UVC to electrical power converting element 181(1), and power supply controller 184 for controlling the charging of a capacitor 182(1) and/or the provision of power from the capacitor.

Figure 9:
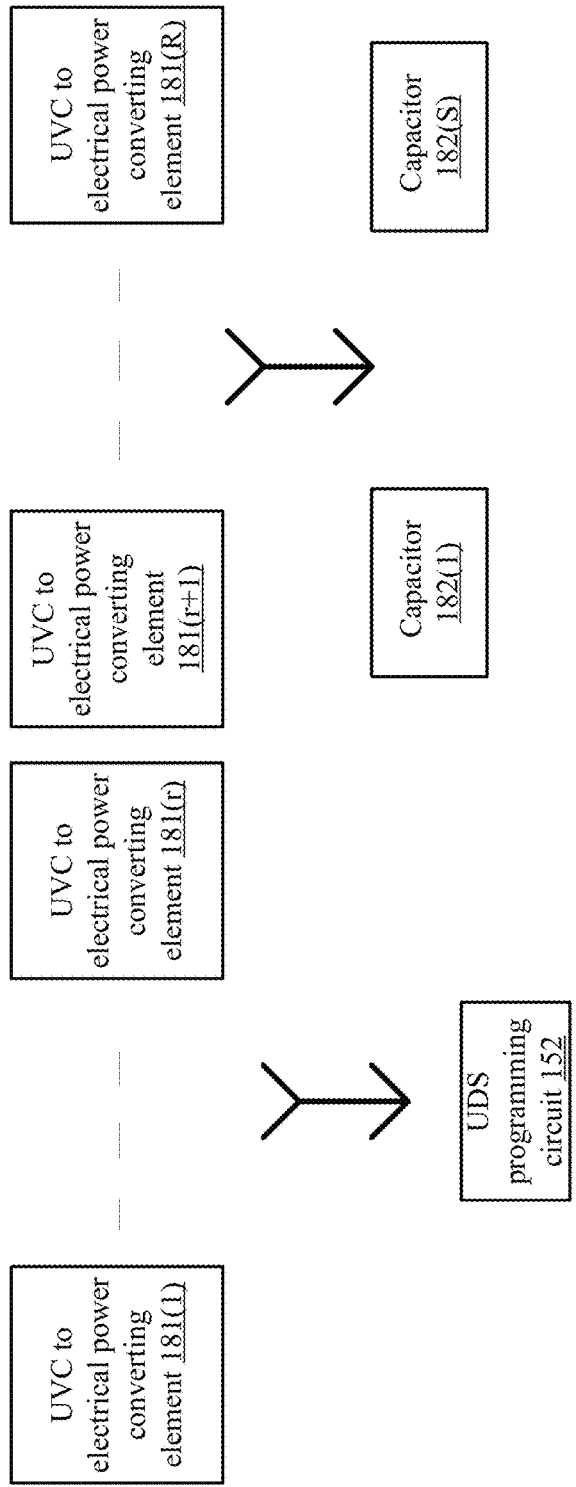
FIG. 9 is an example of a power supply of a node.

FIG. 9 illustrates UVC to electrical power converting elements 181(1)-181(R) and capacitors 182(1)-182(S). R and S are positive integers. In FIG. 7 R and S exceed one—although there may be a single UVC to electrical power converting element and/or a single capacitor. A capacitor is any component configured to store charge.

FIG. 9 illustrates that the UVC to electrical power converting elements include (i) a first set of UVC electrical power converting elements (181(1)-181(r)) that are configured to charge a UDS programming circuit 152, and (ii) a second set of UVC electrical power converting elements (181(r+1)-181(R)) that are configured to change capacitors 182(1)-182(S) for providing power to at least one other component of the node. Value r may range between 1 and R−1. In FIG. 8 the first set and the second set include serially connected UVC to electrical power converting elements—but at least some may be coupled in parallel to each other.

An example of sequences of UVC to electrical power converting elements is illustrated in U.S. Pat. No. 8,344,468 which is incorporated herein by reference.

Figure 10:
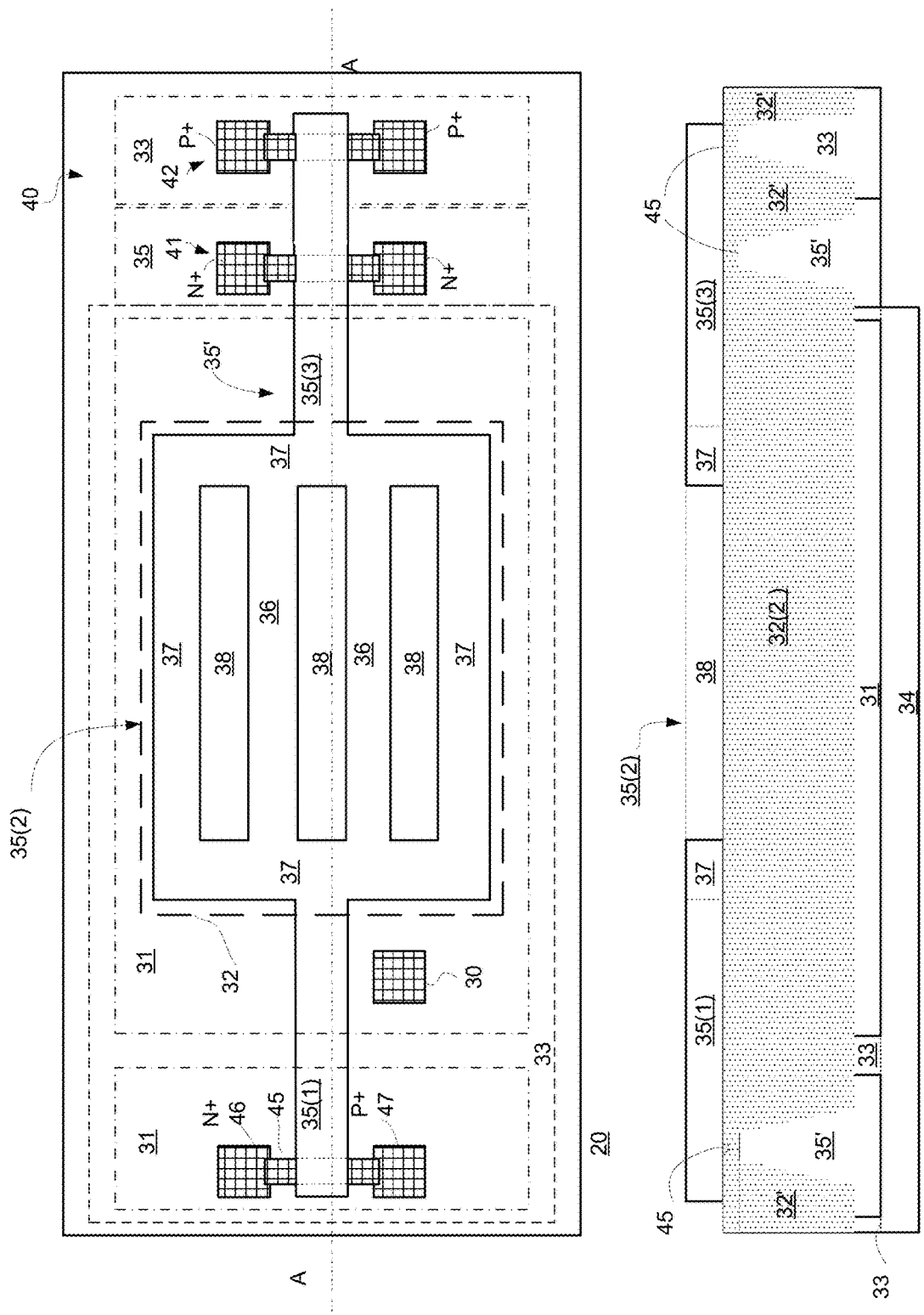
FIG. 10 is an example of a UVC sensing element.

FIG. 10 illustrates an example of a UVC sensing element 20. Examples of UVC sensing elements are illustrated in U.S. patent application Ser. No. 17/444,560 which is incorporated herein by reference.

The top part of FIG. 10 provides a top view of the UVC sensing element while the bottom part of FIG. 10 is a cross sectional view along longitudinal axis A-A.

The UVC sensing element 20 may include an area with a dielectric material 32. The area includes a first portion (also referred to as gate oxide) 45 of a first thickness D1 54 and a second portion 32(2) that is a trench of depth D2 55. The first portion thickness is smaller than the second thickness (trench depth)—for example by a factor of 5, 10, 15 and even more.

The second thickness may ranges between 500 Angstrom and 10000 Angstrom.

The first depth may range between 70 to 150 Angstrom.

The UVC sensing element 20 also includes a floating gate 35 that may include a first floating gate portion 35(1) that is positioned above the first portion 45, and a second floating gate portion 35(2) that is positioned above the second portion of the area with the dielectric material.32(2), wherein the second floating gate portion includes multiple segments (for example external segments 37 and internal segments 36), wherein there are one or more gaps 38 between two or more of the multiple segments.

FIG. 10 illustrates a second portion that has the "grilled" shape that includes a rectangular frame (formed by external segments 37) and internal segments 36 that stretch from one face of the rectangular frame to an opposite facet of the frame—and are parallel to the first and third portions of the floating gate.

The UVC sensing element may also include charging elements for charging the floating gate—such as independently biased control gate 30 and tunneling gate 36' that is illustrated as including tunneling gate—P+ part 46 and tunneling gate—N+ part 47.

The UVC sensing element also includes a readout circuit 40 for reading the floating gate.

In FIG. 10 the readout circuit 40 includes NMOS transistor 41 and PMOS transistor 42. The NMOS transistor 41 may be connected to the PMOS transistor 42 in various manners—for example—by forming an inverter. Alternatively—the NMOS and the PMOS transistors may be coupled in parallel—and when only one is activated at a time—only that activated transistor forms the readout circuit.

The tunneling gates are formed within a P-well 35'— having N-well 33 and dielectric from both sides and deep N-well 34 below.

The NMOS transistor 41 is formed within a P-well 35' and the PMOS transistor is formed within N-well 33. Dielectric isolation (trench filled with dielectric) is also formed at the top between the P-well 35' and the N-well 33, between the NMOS transistor and the left part of the third portion of the floating gate, and between the tunneling gate and the right part of the first portion of the floating gate.

The floating gate may be coupled to control gate and to a tunneling gate (allowing precisely controllable charge injection of both polarities), and to a CMOS inverter. This inverter may include serially connected NMOS and PMOS transfer transistors (allowing different approaches of sensor read-out—logic and analog). In order to enhance sensitivity to UVC radiation, the capacitor may be implemented in the shape of a comb and may use STI dielectric (for example— about 3500 A, much thicker than GOX), to increase the area of the capacitor, thus exposing it to larger number of UVC photons while keeping low capacitance (smaller number of electrons in the FG charged to a given potential). The proposed UVC sensing element may be operated in a range of plus till minus five volts or another voltage range. The UVC sensing element can be implemented in a standard CMOS 0.18 um platform, without a need for special high-voltage devices.

The proposed UVC sensing elements may feature ultra-low power consumption (below 1 uW) in all operation modes—thus, they are suitable for a wide range of application, including passive RFID, or other self-powered systems.

Figure 11:
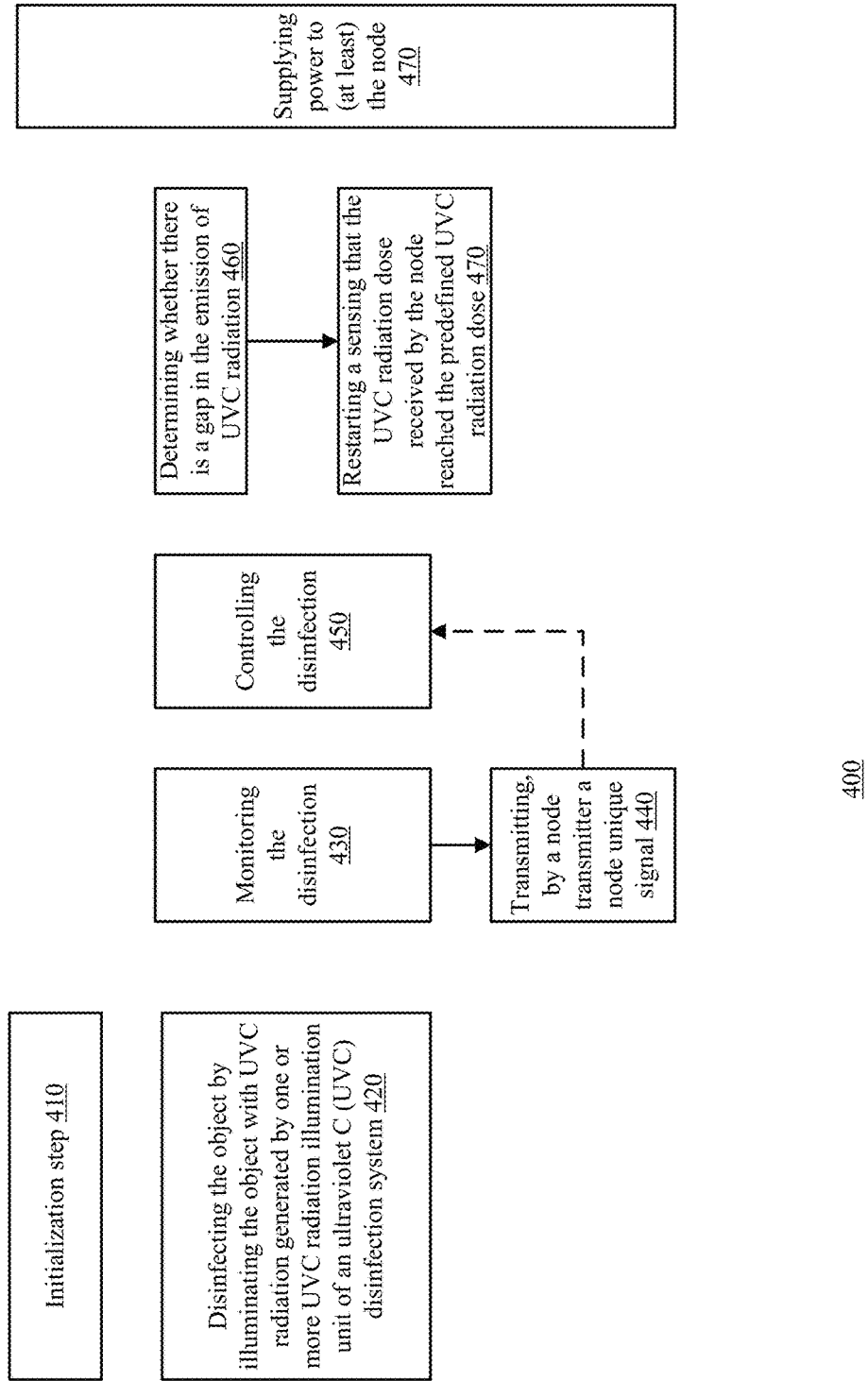
FIG. 11 is an example of a method.

FIG. 11 is an example of a method 400.

Method 400 may start by initialization step 410.

Initialization step may include reaching an object to be disinfected, placing nodes at one or more locations related to the object (if such nodes were not near the object before), and the like.

The object may be a room, a wall, a space, a vehicle, a building, a tool, and the like.

Step 410 may be followed by step 420 of disinfecting the object by illuminating the object with UVC radiation generated by one or more UVC radiation illumination unit of an ultraviolet C (UVC) disinfection system.

Step 420 may include determining to start the disinfection process—especially start to illuminate the object. The determination may be executed in any manner—especially for any manner illustrated above.

Step 420 may also be followed by step 430 of monitoring the disinfection.

Step 430 may include sensing, by a UVC dose sensing unit node (the UVC dose sensing unit node includes a UVC sensing element) that the UVC radiation dose received by the node reached a predefined UVC radiation dose.

Following the sensing that the UVC radiation dose received by the node reached a predefined UVC radiation dose—step 430 is followed by step 440 of transmitting, by a node transmitter a node unique signal following the sensing of step 430.

Method 400 may also include step 450 of controlling the disinfection. Step 450 may be executed in parallel to (at least) steps 420 and 430.

Step 450 may include controlling an emission of UVC radiation from the UVC radiation illumination unit based on a reception or a lack of reception of the node unique signal.

For example—step 450 may include stopping, by a control unit, the UVC radiation emission following a reception of the node unique signal.

Method 400 may also include step 460 of determining whether there is a gap in the emission of UVC radiation of step 420. Especially—step 460 includes determining that a duration of the gap exceeds a threshold and in this case—step 460 may include step 470 of restarting a sensing that the UVC radiation dose received by the node reached the predefined UVC radiation dose.

Step 460 may be executed in parallel to (at least) steps 420, 430.

Step 470 may be a part of step 450 but may be executed independently of step 450.

Method 400 may also include step 470 of supplying power to (at least) components of the node. Step 470 may be executed in parallel to (at least) steps 410, 420, 430, 440, 450 and 460. Step 470 may include converting UVC radiation (or even other radiation such UV that differs from UV, visible light, and the like) to power.

Method 400 may include operating any of the nodes and/or any of the UVC disinfection systems illustrated in the application.

Figure 12:
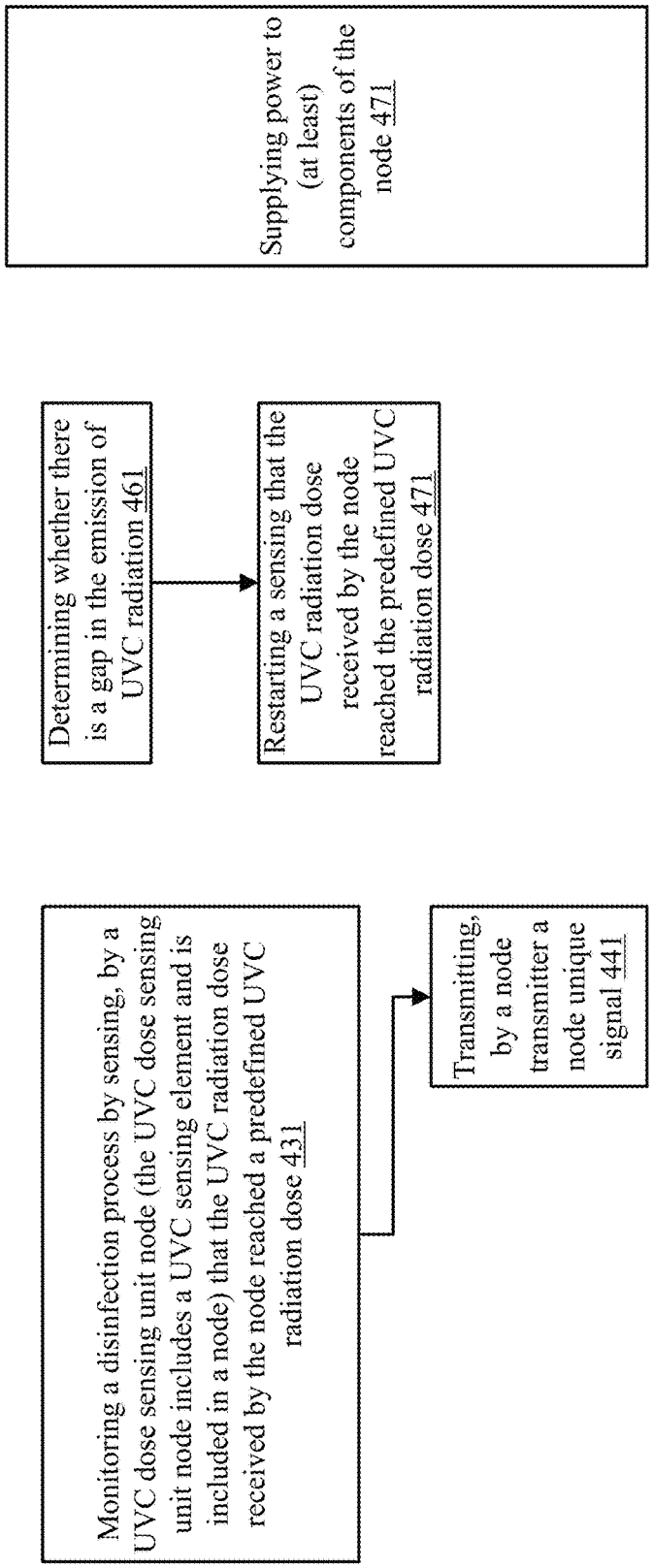
FIG. 12 is an example of a method.

FIG. 12 is an example of a method 401.

Method 401 may start by step 431 of monitoring a disinfection process by sensing, by a UVC dose sensing unit node (the UVC dose sensing unit node includes a UVC sensing element and is included in a node) that the UVC radiation dose received by the node reached a predefined UVC radiation dose.

When the UVC radiation dose received by the node reaches a predefined UVC radiation dose—step 431 is followed by step 441 of transmitting, by a node transmitting a node unique signal following the sensing of step 430.

Method 401 may also include step 461 of determining whether there is a gap in the emission of UVC radiation. Especially—step 461 includes determining that a duration of the gap exceeds a threshold and in this case—step 461 may include step 471 of restarting a sensing that the UVC radiation dose received by the node reached the predefined UVC radiation dose.

Step 461 may be executed in parallel to (at least) step 431.

Method 401 may also include step 471 of supplying power to (at least) components of the node. Step 471 may be executed in parallel to (at least) steps 431, 441 and 461. Step 471 may include converting UVC radiation (or even other radiation: UV that differs from UVC, visible light, and the like) to power.

Method 401 may include operating any of the nodes illustrated in the application.

Any reference to any of the terms "comprise", "comprises", "comprising" "including", "may include" and "includes" may be applied, mutatis mutandis, to any of the terms "consists", "consisting", "consisting essentially of".

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. An ultraviolet C (UVC) disinfection system comprising:
   a UVC radiation illumination unit;
   a control unit; and
   a node that comprises:
      a power supply;
      a UVC dose sensing unit that comprises a UVC sensing element, wherein the UVC dose sensing unit is configured to sense that the UVC radiation dose received by the node reached a predefined UVC radiation dose; and
      a node transmitter that is configured to transmit a node unique signal following a sensing, by the UVC dose sensing unit, that the UVC radiation dose received by the node reached the predefined UVC radiation dose; and
   wherein the control unit is configured to control an emission of UVC radiation from the UVC radiation illumination unit based on a reception or a lack of reception of the node unique signal.

2. The UVC disinfection system according to claim 1 wherein the control unit is configured to stop the UVC radiation emission following the reception of the node unique signal.

3. The UVC disinfection system according to claim 1 wherein the node unique signal is a node identifier.

4. The UVC disinfection system according to claim 1 wherein the node comprises a gap detection circuit that is configured to detect a gap in the emission of UVC radiation.

5. The UVC disinfection system according to claim 4 wherein the node comprises a node controller that is configured to:
   determine that a duration of the gap exceeds a threshold and to restart a sensing that the UVC radiation dose received by the node reached the predefined UVC radiation dose.

6. The UVC disinfection system according to claim 5 wherein the gap detection circuit comprises a gap detection sensing element that comprises a gap detection floating gate (FG) component, and a gap detection reference sensing element that comprises a gap detection reference FG component;
   wherein a charge retention of the gap detection FG component is higher than a charge retention of the gap detection reference FG component; and
   wherein the gap detection FG component is ignorant to the UVC radiation.

7. The UVC disinfection system according to claim 6 wherein the UVC disinfection system is configured to determine that the duration of the gap exceeds the threshold based on a difference between a potential of a gap detection FG of a gap detection FG component and a potential of a gap detection reference FG of the gap detection reference FG component.

8. The UVC disinfection system according to claim 4 wherein the gap detection circuit comprises a gap detection reference sensing element that comprises a gap detection reference floating gate (FG) that is coupled to a metal layer of the gap detection circuit.

9. The UVC disinfection system according to claim 1 wherein the UVC dose sensing unit further comprises a comparator;
   wherein the UVC sensing element comprises a floating gate (FG);
   wherein the comparator is configured to (i) compare a voltage that is indicative of a FG potential to a reference voltage, and (ii) to output a comparator output signal that is indicative that the FG potential reached the reference potential when the UVC sensing unit was exposed to the predefined UVC radiation dose; and
   wherein the node transmitter is configured transmit the node unique signal following a generation of the comparator output signal that is indicative that the FG potential reached the reference potential.

10. The UVC disinfection system according to claim 1 wherein the node transmitter is an RFID transmitter, wherein the node unique signal is an RFID code; and
    wherein the UVC disinfection system comprises a RFID reader that is in communication with the control unit.

11. The UVC disinfection system according to claim 1 wherein the power supply is a UVC radiation based power supply that is configured to convert UVC radiation to electrical power.

12. The UVC disinfection system according to claim 11 wherein the UVC radiation based power supply comprises one or more UVC to electrical power converting elements and one or more capacitors.

13. The UVC disinfection system according to claim 12 wherein the one or more UVC electrical power converting elements are multiple UVC electrical power converting elements.

14. The UVC disinfection system according to claim 13 wherein the multiple UVC electrical power converting elements comprises:
    a first set of UVC electrical power converting elements that are configured to charge a floating gate programming circuit of the node; and
    a second set of UVC electrical power converting elements that are configured to power at least one other component of the node.

15. The UVC disinfection system according to claim 14 wherein the floating gate programming circuit is configured to program a floating gate (FG) potential to have predefined potential value at a start of a sensing period during which the UVC dose sensing unit is configured to sense that the UVC radiation dose received by the node reached the predefined UVC radiation dose.

16. The UVC disinfection system according to claim 12 wherein the node comprises a system on chip (SoC), and wherein the one or more capacitors are bonded to the SoC.

17. The UVC disinfection system according to claim 12 wherein the node comprises a system on chip (SoC), and wherein the one or more capacitors belong to the SoC.

18. The UVC disinfection system according to claim 1 wherein the node is a first node;
- wherein the UVC disinfection comprises a group of nodes, wherein the group comprises the first node;
- wherein each node of the group is configured to transmit a node unique signal following a sensing, by a UVC dose sensing unit of the node, that the UVC radiation dose received by the node reached the predefined UVC radiation dose;
- wherein different nodes of the group are configured to transmit node unique signals that differ from each other; and
- wherein the control unit is configured to control the emission of UVC radiation from the UVC radiation illumination unit based on a reception or a lack of reception of node unique signals from at least some of the nodes of the group.

19. An ultraviolet C (UVC) node, comprising:
- a power supply;
- a UVC dose sensing unit that comprises a UVC sensing element, wherein the UVC dose sensing unit is configured to sense that a UVC radiation dose received by the node reached a predefined UVC radiation dose; and
- a node transmitter that is configured transmit a node unique signal following a sensing, by the UVC dose sensing unit, that the UVC radiation dose received by the node reached the predefined UVC radiation dose.

20. A method for ultraviolet C (UVC) disinfection, the method comprises:
- sensing, by a UVC dose sensing unit of a node, that a UVC radiation dose received by the node reached a predefined UVC radiation dose; wherein the UVC dose sensing unit comprises a UVC sensing element; and
- transmitting, by a node transmitter of the node, a node unique signal following the sensing, by the UVC dose sensing unit, that the UVC radiation dose received by the node reached the predefined UVC radiation dose.

\* \* \* \* \*